United States Patent
Stahmann et al.

(10) Patent No.: US 9,675,811 B2
(45) Date of Patent: Jun. 13, 2017

(54) DISPLAY OF TEMPORALLY ALIGNED HEART INFORMATION FROM SEPARATE IMPLANTABLE MEDICAL DEVICES ON AN EXTRACORPOREAL DISPLAY

(71) Applicant: CARDIAC PACEMAKERS, INC., St. Paul, MN (US)

(72) Inventors: Jeffrey E. Stahmann, Ramsey, MN (US); Michael J. Kane, Roseville, MN (US); Paul Huelskamp, St. Paul, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/835,250

(22) Filed: Aug. 25, 2015

(65) Prior Publication Data
US 2016/0059024 A1 Mar. 3, 2016

Related U.S. Application Data

(60) Provisional application No. 62/043,086, filed on Aug. 28, 2014.

(51) Int. Cl.
| | |
|---|---|
| *A61N 1/00* | (2006.01) |
| *A61N 1/39* | (2006.01) |
| *A61N 1/375* | (2006.01) |
| *A61B 5/0404* | (2006.01) |
| *A61B 5/042* | (2006.01) |
| *A61B 5/044* | (2006.01) |

(Continued)

(52) U.S. Cl.
CPC ............ *A61N 1/3962* (2013.01); *A61B 5/042* (2013.01); *A61B 5/044* (2013.01); *A61B 5/0404* (2013.01); *A61N 1/3621* (2013.01); *A61N 1/3702* (2013.01); *A61N 1/3756* (2013.01); *A61N 1/37235* (2013.01); *A61N 1/3925* (2013.01); *A61B 5/02* (2013.01); *A61N 1/37247* (2013.01); *A61N 1/37288* (2013.01)

(58) Field of Classification Search
CPC .. A61N 1/3962; A61N 1/3621; A61N 1/3702; A61N 1/37235; A61N 1/3756; A61N 1/3925; A61B 5/0404; A61B 5/042; A61B 5/044
See application file for complete search history.

(56) References Cited

U.S. PATENT DOCUMENTS

| | | | |
|---|---|---|---|
| 6,694,179 B1 * | 2/2004 | Mouchawar | ............ A61B 5/044 600/523 |
| 8,340,750 B2 | 12/2012 | Prakash et al. | |

(Continued)

FOREIGN PATENT DOCUMENTS

JP 5199867 B2 2/2013

*Primary Examiner* — Scott Getzow
(74) *Attorney, Agent, or Firm* — Seager, Tufte & Wickhem LLP.

(57) ABSTRACT

A cardiac rhythm management system includes a first implantable device such as a defibrillator and a second implantable device such as a leadless cardiac pacemaker. A programmer is configured to receive and display heart data emanating from the implantable defibrillator and from the leadless cardiac pacemaker. The heart data emanating from the leadless cardiac pacemaker is displayed in temporal alignment with the heart data emanating from the implantable defibrillator.

17 Claims, 12 Drawing Sheets

(51) Int. Cl.
*A61N 1/362* (2006.01)
*A61N 1/372* (2006.01)
*A61N 1/37* (2006.01)
*A61B 5/02* (2006.01)

(56) References Cited

U.S. PATENT DOCUMENTS

| | | |
|---|---|---|
| 8,571,678 B2 | 10/2013 | Wang |
| 8,676,335 B2 | 3/2014 | Katoozi et al. |
| 8,744,572 B1 | 6/2014 | Greenhut et al. |
| 8,747,314 B2 | 6/2014 | Stahmann et al. |
| 2006/0241725 A1* | 10/2006 | Libbus ................ A61B 5/0006 607/60 |
| 2008/0130670 A1 | 6/2008 | Kim et al. |
| 2008/0140140 A1* | 6/2008 | Grimley ............... A61N 1/3925 607/5 |
| 2009/0048646 A1 | 2/2009 | Katoozi et al. |
| 2009/0171414 A1 | 7/2009 | Kelly et al. |
| 2010/0013668 A1 | 1/2010 | Kantervik |
| 2010/0168819 A1 | 7/2010 | Freeberg |
| 2013/0085403 A1 | 4/2013 | Gunderson et al. |
| 2014/0169162 A1 | 6/2014 | Romano et al. |
| 2014/0214104 A1* | 7/2014 | Greenhut ........... A61N 1/37288 607/4 |

\* cited by examiner

DISPLAY OF TEMPORALLY ALIGNED HEART INFORMATION FROM SEPARATE IMPLANTABLE MEDICAL DEVICES ON AN EXTRACORPOREAL DISPLAY

CROSS REFERENCE TO RELATED APPLICATIONS

This application claims the benefit of U.S. Provisional Patent Application Ser. No. 62/043,086 filed Aug. 28, 2014, the disclosures of each incorporated herein by reference.

TECHNICAL FIELD

The present disclosure generally relates to implantable medical devices and more particularly to methods and systems for displaying information from implantable medical devices on an extracorporeal display.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices that are configured to communicate information between the devices. In some instances, such as during a physician visit, it would be desirable to display temporally aligned heart information from each of the implantable devices on an extracorporeal display.

SUMMARY

The present disclosure generally relates to implantable medical devices and more particularly to methods and systems for displaying temporally aligned heart information from two or more implantable medical devices on an extracorporeal display.

In a first example, a cardiac rhythm management system may include an implantable defibrillator configured to monitor a patient's heart and provide shocking therapy if appropriate, and a leadless cardiac pacemaker configured to sense the patient's heart and provide pacing therapy if appropriate. A programmer may be configured to receive and display temporal heart data emanating from the implantable defibrillator and from the leadless cardiac pacemaker. The temporal heart data emanating from the leadless cardiac pacemaker may be displayed in temporal alignment with the heart data emanating from the implantable defibrillator on the display of the programmer. In some cases, the heart data emanating from the implantable defibrillator and the heart data emanating from the leadless cardiac pacemaker each identify the occurrence of one or more temporal events.

Alternatively, or additionally, and in a second example, the heart data of the first example, emanating from the implantable defibrillator and/or the leadless cardiac pacemaker, is displayed by the programmer in real or near real time.

Alternatively, or additionally, and in a third example, the heart data of the first example, emanating from the implantable defibrillator and/or the leadless cardiac pacemaker, is stored data and the stored data is displayed at a later time.

Alternatively, or additionally, and in a fourth example, the heart data of any of the first through third examples, emanating from the leadless cardiac pacemaker, is communicated to the programmer via the implantable defibrillator.

Alternatively, or additionally, and in a fifth example, the heart data of any of the first through fourth examples, emanating from the implantable defibrillator, includes at least a portion of an electrocardiogram.

Alternatively, or additionally, and in a sixth example, the heart data of any of the first through fifth examples, emanating from the leadless cardiac pacemaker, includes a plurality of markers.

Alternatively, or additionally, and in a seventh example, the heart data of any of the first through sixth examples, emanating from the implantable defibrillator, includes a number of first time stamps.

Alternatively, or additionally, and in an eighth example, the heart data of any of the first through seventh examples, emanating from the leadless cardiac pacemaker, includes a number of second time stamps.

Alternatively, or additionally, and in a ninth example, the programmer of the eighth example is configured to use the first and second time stamps to temporally align the heart data emanating from the implantable defibrillator and the heart data emanating from the leadless cardiac pacemaker.

Alternatively, or additionally, and in a tenth example, the programmer of any of the first through eighth examples in which the programmer is configured to utilize one or more user-defined time delay parameters to temporally align the heart data emanating from the implantable defibrillator and the heart data emanating from the leadless cardiac pacemaker.

Example eleven is a cardiac rhythm management system including a first implantable device, a second implantable device and a programmer in communication with the first implantable device and the second implantable device. In some embodiments, the first implantable device may be an implantable defibrillator and the second implantable device may be a leadless cardiac pacemaker as in examples one through ten, but this is not required. The programmer is configured to receive and display heart data collected by the first implantable device and heart data collected by the second implantable device, wherein the heart data collected by the first implantable device and the heart data collected by the second implantable device each identify the occurrence of one or more temporal events. The programmer displays the heart data collected by the second device in temporal alignment with the heart data collected by the first device.

Alternatively, or additionally, and in a twelfth example, the programmer of the eleventh example is further configured to display the heart data collected by the first implantable device and the second implantable device in real or near real time.

Alternatively, or additionally, and in a thirteenth example, the heart data of the eleventh example collected by the first implantable device and/or the heart data collected by the second implantable device is stored data, and the stored heart data collected by the first implantable device and/or the stored heart data collected by the second implantable device is displayed at a later time.

Alternatively, or additionally, and in a fourteenth example, the heart data of any of the eleventh through thirteenth examples, collected by the first implantable device, includes at least a portion of an electrocardiogram.

Alternatively, or additionally, and in a fifteenth example, the heart data of any of the eleventh through fourteenth example, collected by the second device, includes a plurality of markers.

Alternatively, or additionally, and in a sixteenth example, the heart data of any of the eleventh through fifteenth examples, collected by the first implantable device and/or the second implantable device, includes a plurality of time stamps, and the programmer is configured to use the plurality of time stamps to temporally align the heart data collected by the first implantable device and the heart data collected by the second implantable device.

Alternatively, or additionally, and in a seventeenth example, the programmer of any of the eleventh through fifteenth examples is configured to utilize one or more user-defined time delay parameters to temporally align the heart data collected by the first implantable device and the heart data collected by the second implantable device.

Example eighteen is a method of comparing heart rhythm data from a plurality of implantable medical devices. Heart data emanating from a first implantable device that is configured to monitor a patient's heart is received. Heart data emanating from a second implantable device that is configured to monitor the patient's heart is received. The heart data emanating from the second implantable device is temporally offset from the heart data emanating from the first implantable device. The heart data emanating from the first implantable device is temporally aligned with the heart data emanating from the second implantable device and the temporally aligned heart data is displayed on a display.

Alternatively, or additionally, and in a nineteenth example, in the method of the eighteenth example, temporally aligning the heart data emanating from the first implantable device with the heart data emanating from the second implantable device includes using time stamp data included with either the heart data emanating from the first implantable device, the heart data emanating from the second implantable device, or both.

Alternatively, or additionally, and in a twentieth example, in the method of any of the eighteenth or nineteenth examples, temporally aligning the heart data emanating from the first implantable device with the heart data emanating from the second implantable device includes using a user-defined delay value for heart data emanating from the second implantable device.

Alternatively, or additionally, and in a twenty first example, in the method of any of the eighteenth through twentieth examples in which displaying the temporally aligned heart data includes displaying at least a portion of an electrocardiogram emanating from the first implantable device and one or more markers emanating from the second implantable device.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
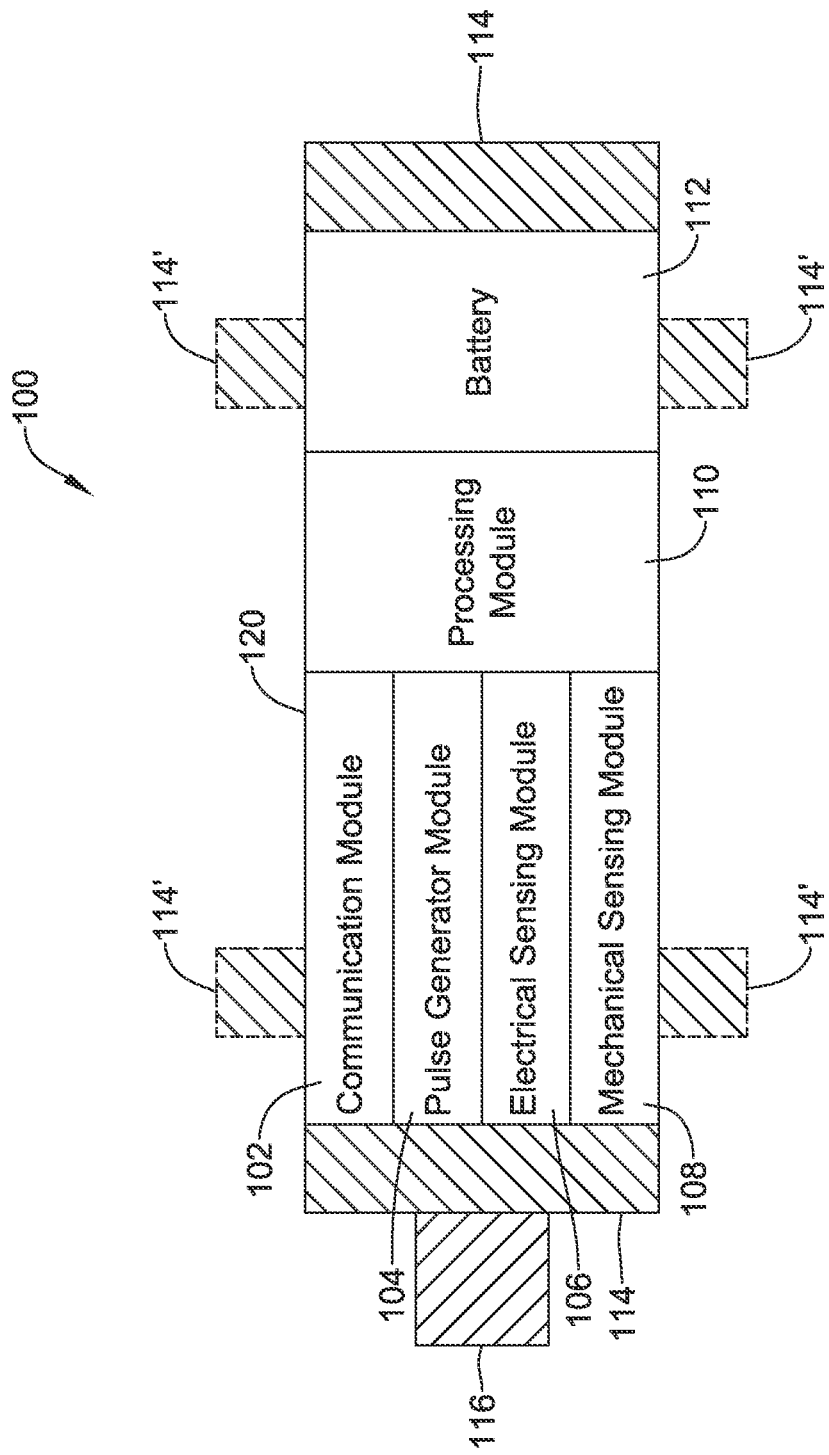
FIG. 1 is a schematic block diagram of an illustrative leadless cardiac pacemaker (LCP) according to an example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical device which may be configured to determine occurrences of such cardiac abnormalities or arrhythmias and deliver one or more types of electrical stimulation therapy to patient's hearts may help to terminate or alleviate such cardiac conditions.

FIG. 1 depicts an exemplary leadless cardiac pacemaker (LCP) that may be implanted into a patient and may operate to prevent, control, or terminate cardiac arrhythmias in patients, for example by appropriately employing one or more therapies (e.g. anti-tachycardia pacing (ATP) therapy, cardiac resynchronization therapy (CRT), bradycardia therapy, defibrillation pulses, or the like). As can be seen in FIG. 1, LCP 100 may be a compact device with all components housed within LCP 100 or directly on housing 120. In the example shown in FIG. 1, LCP 100 may include a communication module 102, a pulse generator module 104, an electrical sensing module 106, a mechanical sensing module 108, a processing module 110, a battery 112, and electrodes 114. LCP 100 may include more or less modules, depending on the application.

Communication module 102 may be configured to communicate with devices such as sensors, other medical devices, and/or the like, that are located externally to LCP 100. Such devices may be located either external or internal to the patient's body. Irrespective of the location, external devices (i.e. external to the LCP 100 but not necessarily external to the patient's body) can communicate with LCP 100 via communication module 102 to accomplish one or more desired functions. For example, LCP 100 may communicate information, such as sensed electrical signals, data, instructions, messages, etc., to an external medical device through communication module 102. The external medical device may use the communicated signals, data, instructions and/or messages to perform various functions, such as determining occurrences of arrhythmias, delivering electrical stimulation therapy, storing received data, displaying received data, and/or performing any other suitable function. LCP 100 may additionally receive information such as signals, data, instructions and/or messages from the external medical device through communication module 102, and LCP 100 may use the received signals, data, instructions and/or messages to perform various functions, such as determining occurrences of arrhythmias, delivering electrical stimulation therapy, storing received data, and/or performing any other suitable function. Communication module 102 may be configured to use one or more methods for communicating with external devices. For example, communication module 102 may communicate via radiofrequency (RF) signals, inductive coupling, optical signals, acoustic signals, conducted communication signals, and/or any other signals suitable for communication.

In the example shown in FIG. 1, pulse generator module 104 may be electrically connected to electrodes 114. In some examples, LCP 100 may additionally include electrodes 114'. In such examples, pulse generator 104 may also be electrically connected to electrodes 114'. Pulse generator module 104 may be configured to generate electrical stimulation signals. For example, pulse generator module 104 may generate electrical stimulation signals by using energy stored in battery 112 within LCP 100 and deliver the generated electrical stimulation signals via electrodes 114 and/or 114'. Alternatively, or additionally, pulse generator 104 may include one or more capacitors, and pulse generator 104 may charge the one or more capacitors by drawing energy from battery 112. Pulse generator 104 may then use the energy of the one or more capacitors to deliver the generated electrical stimulation signals via electrodes 114 and/or 114'. In at least some examples, pulse generator 104 of LCP 100 may include switching circuitry to selectively connect one or more of electrodes 114 and/or 114' to pulse generator 104 in order to select which electrodes 114/114' (and/or other electrodes) pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, LCP 100 may not include a pulse generator 104. For example, LCP 100 may be a diagnostic only device. In such examples, LCP 100 may not deliver electrical stimulation therapy to a patient. Rather, LCP 100 may collect data about cardiac electrical activity and/or physiological parameters of the patient and communicate such data and/or determinations to one or more other medical devices via communication module 102.

In some examples, LCP 100 may include an electrical sensing module 106, and in some cases, a mechanical sensing module 108. Electrical sensing module 106 may be configured to sense the cardiac electrical activity of the heart. For example, electrical sensing module 106 may be connected to electrodes 114/114', and electrical sensing module 106 may be configured to receive cardiac electrical signals conducted through electrodes 114/114'. The cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. Mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical/chemical parameters of the patient. Both electrical sensing module 106 and mechanical sensing module 108 may be connected to a processing module 110, which may provide signals representative of the sensed mechanical parameters. Although described with respect to FIG. 1 as separate sensing modules, in some cases, electrical sensing module 106 and mechanical sensing module 108 may be combined into a single sensing module, as desired. In addition to, or instead of, electrical sensing module 106 and/or mechanical sensing module 108, LCP 100 may include other types of sensing modules such as a magnetic sensing module, a chemical sensing module and/or a nuclear sensing module.

Electrodes 114/114' can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114/114' may be supported by the housing 120, although in some examples, electrodes 114/114' may be connected to housing 120 through short connecting wires such that electrodes 114/114' are not directly secured relative to housing 120. In examples where LCP 100 includes one or more electrodes 114', electrodes 114' may in some cases be disposed on the sides of LCP 100, which may increase the number of electrodes by which LCP 100 may sense cardiac electrical activity, deliver electrical stimulation and/or communicate with an external medical device. Electrodes 114/114' can be made up of one or more biocompatible conductive materials such as various metals or alloys that are known to be safe for implantation within a human body. In some instances, electrodes 114/114' connected to LCP 100 may have an insulative portion that electrically isolates electrodes 114/114' from adjacent electrodes, housing 120, and/or other parts of the LCP 100.

Processing module 110 can be configured to control the operation of LCP 100. For example, processing module 110 may be configured to receive electrical signals from electrical sensing module 106 and/or mechanical sensing module 108. Based on the received signals, processing module 110 may determine, for example, occurrences and, in some cases, types of arrhythmias. Based on any determined arrhythmias, processing module 110 may control pulse generator module 104 to generate electrical stimulation in accordance with one or more therapies to treat the determined arrhythmia(s). Processing module 110 may further receive information from communication module 102. In some examples, processing module 110 may use such received information to help determine whether an arrhythmia is occurring, determine a type of arrhythmia, and/or to take particular action in response to the information. Processing module 110 may additionally control communication module 102 to send/receive information to/from other devices.

In some examples, processing module 110 may include a pre-programmed chip, such as a very-large-scale integration (VLSI) chip and/or an application specific integrated circuit (ASIC). In such embodiments, the chip may be pre-programmed with control logic in order to control the operation of LCP 100. By using a pre-programmed chip, processing module 110 may use less power than other programmable circuits (e.g. general purpose programmable microprocessors) while still being able to maintain basic functionality, thereby potentially increasing the battery life of LCP 100. In other examples, processing module 110 may include a programmable microprocessor. Such a programmable microprocessor may allow a user to modify the control logic of LCP 100 even after implantation, thereby allowing for greater flexibility of LCP 100 than when using a pre-programmed ASIC. In some examples, processing module 110 may further include a memory, and processing module 110 may store information on and read information from the memory. In other examples, LCP 100 may include a separate memory (not shown) that is in communication with processing module 110, such that processing module 110 may read and write information to and from the separate memory.

Battery 112 may provide power to the LCP 100 for its operations. In some examples, battery 112 may be a non-rechargeable lithium-based battery. In other examples, a non-rechargeable battery may be made from other suitable materials, as desired. Because LCP 100 is an implantable device, access to LCP 100 may be limited after implantation. Accordingly, it is desirable to have sufficient battery capacity to deliver therapy over a period of treatment such as days, weeks, months, years or even decades. In some instances, battery 112 may a rechargeable battery, which may help increase the useable lifespan of LCP 100. In still other examples, battery 112 may be some other type of power source, as desired.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

Figure 2:
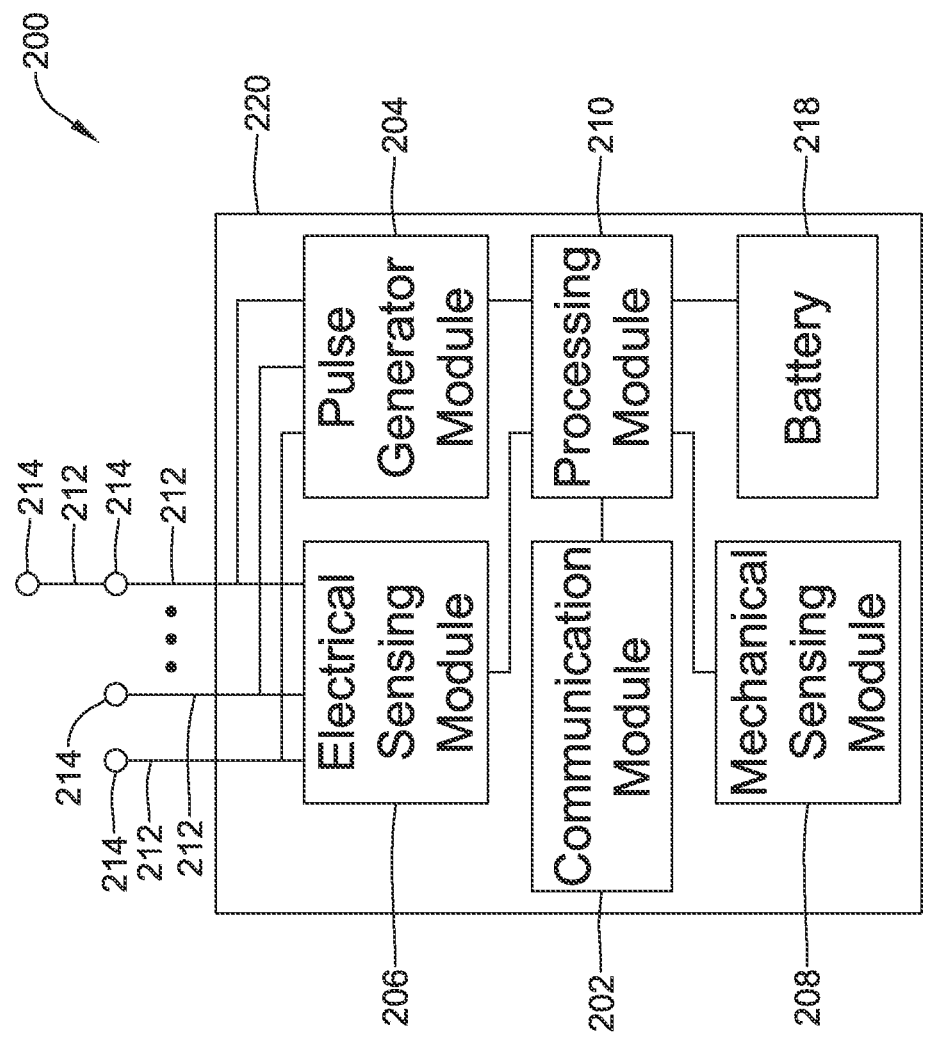
FIG. 2 is a schematic block diagram of another illustrative medical device that may be used in conjunction with the LCP of FIG. 1.

FIG. 2 depicts an example of another medical device (MD) 200, which may be used in conjunction with LCP 100 (FIG. 1) in order to detect and/or treat cardiac arrhythmias and other heart conditions. In the example shown, MD 200 may include a communication module 202, a pulse generator module 204, an electrical sensing module 206, a mechanical sensing module 208, a processing module 210, and a battery 218. Each of these modules may be similar to modules 102, 104, 106, 108, and 110 of LCP 100. Additionally, battery 218 may be similar to battery 112 of LCP 100. In some examples, however, MD 200 may have a larger volume within housing 220. In such examples, MD 200 may include a larger battery and/or a larger processing module 210 capable of handling more complex operations than processing module 110 of LCP 100.

While it is contemplated that MD 200 may be another leadless device such as shown in FIG. 1, in some instances MD 200 may include leads such as leads 212. Leads 212 may include electrical wires that conduct electrical signals between electrodes 214, housing 220, and/or one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212, and in some cases at various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously but adjacent the patient's heart. In some cases, electrodes 214 may conduct intrinsically generated electrical signals to leads 212, e.g. signals representative of intrinsic cardiac electrical activity. Leads 212 may, in turn, conduct the received electrical signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical signals and delivery the signals to the patient's heart (either directly or indirectly).

Mechanical sensing module 208, as with mechanical sensing module 108, may contain or be electrically connected to one or more sensors, such as accelerometers, blood pressure sensors, heart sound sensors, blood-oxygen sensors, and/or other sensors which are configured to measure one or more mechanical/chemical parameters of the heart and/or patient. In some examples, one or more of the sensors may be located on leads 212, but this is not required. In some examples, one or more of the sensors may be located in or on housing 220.

While not required, in some examples, MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body.

In some cases, MD 200 may be an implantable cardiac pacemaker (ICP). In this example, MD 200 may have one or more leads, for example leads 212, which are implanted on or within the patient's heart. The one or more leads 212 may include one or more electrodes 214 that are in contact with cardiac tissue and/or blood within the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured provide defibrillation therapy.

In some instances, MD 200 may be an implantable cardioverter-defibrillator (ICD). In such examples, MD 200 may include one or more leads implanted within a patient's heart. MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously, but this is not required.

In some examples, MD 200 may not be an implantable medical device. Rather, MD 200 may be a device external to the patient's body, and may include skin-electrodes that are placed on a patient's body. In such examples, MD 200 may be able to sense surface electrical signals (e.g. cardiac electrical signals that are generated by the heart or electrical signals generated by a device implanted within a patient's body and conducted through the body to the skin). In such examples, MD 200 may be configured to deliver various types of electrical stimulation therapy, including, for example, defibrillation therapy.

Figure 3:
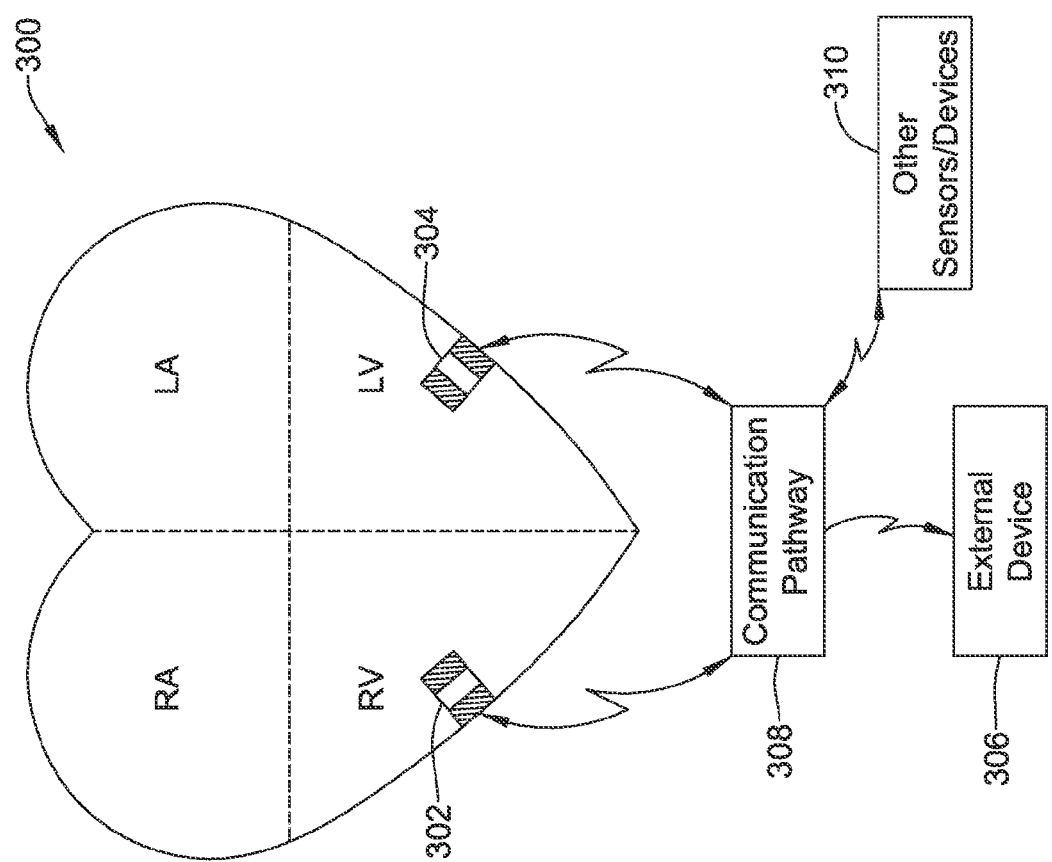
FIG. 3 is a schematic diagram of an exemplary medical system that includes multiple LCPs and/or other devices in communication with one another.

FIG. 3 illustrates an example of a medical device system and a communication pathway through which multiple medical devices 302, 304, 306, and/or 310 may communicate. In the example shown, medical device system 300 may include LCPs 302 and 304, external medical device 306, and other sensors/devices 310. External device 306 may be any of the devices described previously with respect to MD 200. Other sensors/devices 310 may also be any of the devices described previously with respect to MD 200. In some instances, other sensors/devices 310 may include a sensor, such as an accelerometer or blood pressure sensor, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. It is contemplated that communication pathway 308 may communicate using RF signals, inductive coupling, optical signals, acoustic signals, or any other signals suitable for communication. Additionally, in at least some examples, device communication pathway 308 may comprise multiple signal types. For instance, other sensors/device 310 may communicate with external device 306 using a first signal type (e.g. RF communication) but communicate with LCPs 302/304 using a second signal type (e.g. conducted communication). Further, in some examples, communication between devices may be limited. For instance, as described above, in some examples, LCPs 302/304 may communicate with external device 306 only through other sensors/devices 310, where LCPs 302/304 send signals to other sensors/devices 310, and other sensors/devices 310 relay the received signals to external device 306.

In some cases, communication pathway 308 may include conducted communication. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

In some cases, communication pathway 308 may function solely as a communication pathway. In other cases, communication pathway 308 may also perform sensing and/or therapy functions.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
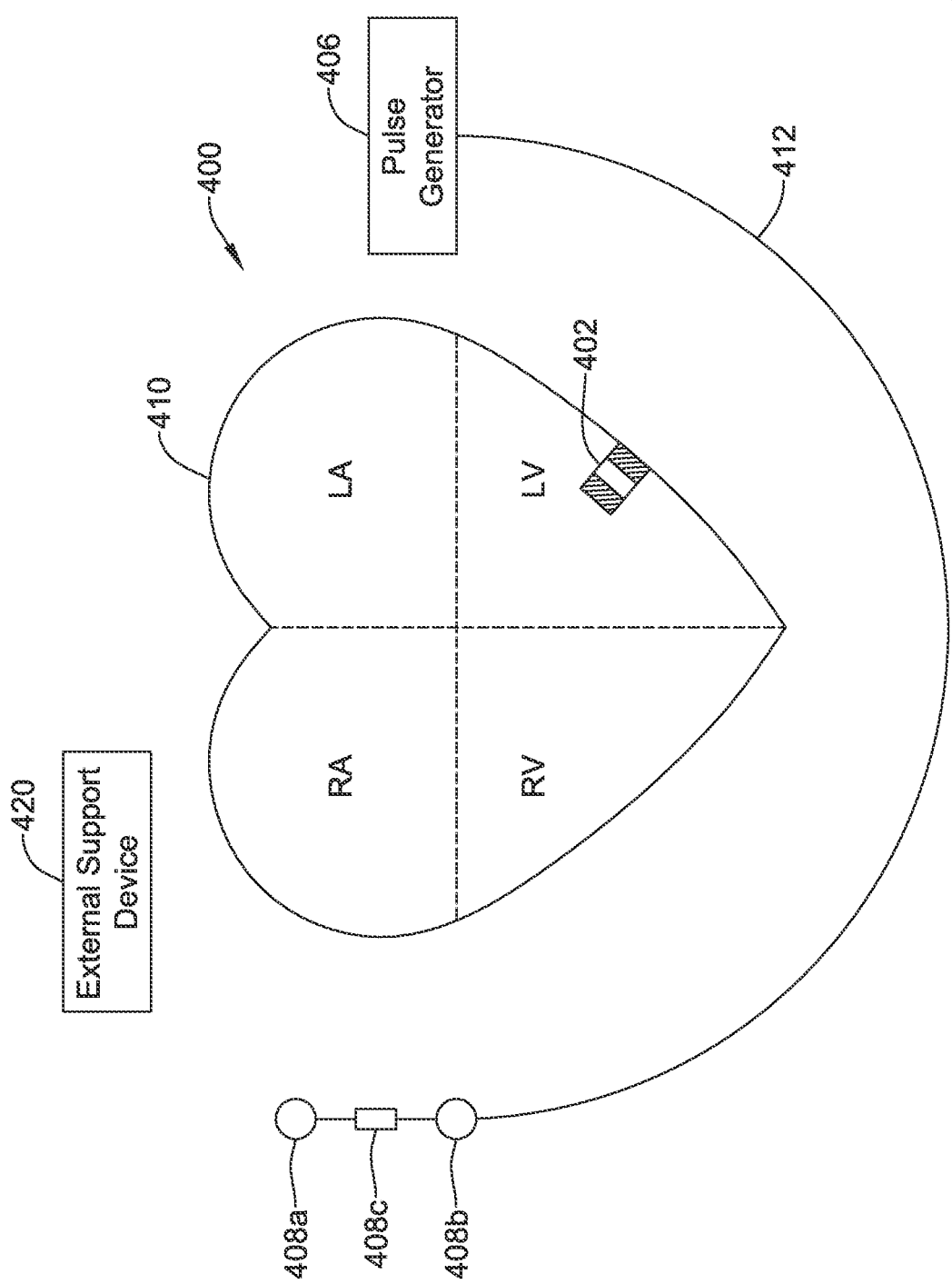
FIG. 4 is a schematic diagram of a system including an LCP and another medical device, in accordance with an example of the present disclosure.
Figure 5:
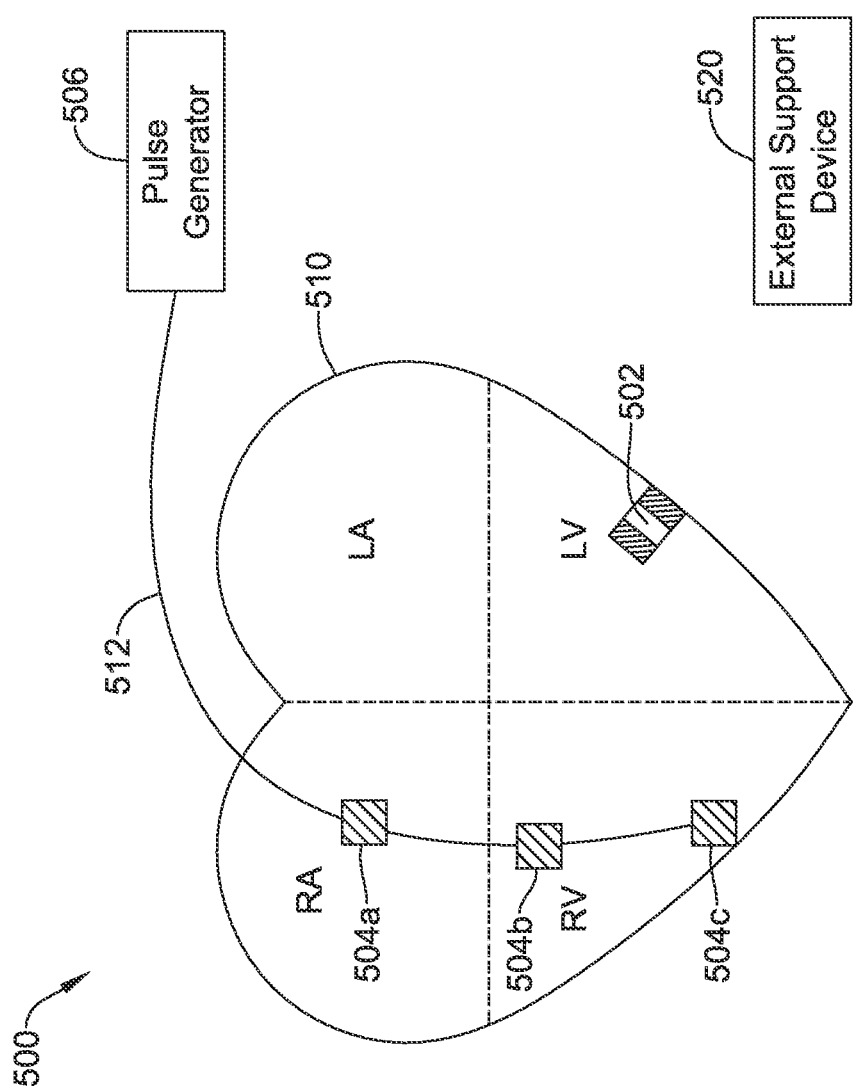
FIG. 5 is a schematic diagram of a system including an LCP and another medical device, in accordance with an example of the present disclosure.

FIGS. 4 and 5 show illustrative medical device systems that may be configured to operate according to techniques disclosed herein. In FIG. 4, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously adjacent the heart. In some cases, the LCP 402 may communicate with the subcutaneous implantable cardioverter-defibrillator (S-ICD). In some cases, the LCP 402 may be in the right ventricle, right atrium or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart. In a further example, one or more LCPs may be implanted on an interior wall of the heart and one or more LCPs may be implanted on an exterior wall of the heart.

In FIG. 5, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted mode. In some examples, communication between the LCP 402 and external support device 420 is accomplished by sending communication information through the pulse generator 406. However, in other examples, communication between the LCP 402 and external support device 420 may be via a communication module.

FIGS. 4-5 only illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as pulse generator 406 or 506, with at least one LCP capable of delivering defibrillation therapy. In yet other examples, the configuration or placement of the medical devices, leads, and/or electrodes may be different from those depicted in FIGS. 6 and 7. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

It will be appreciated that the implantable devices described herein, including but not limited to LCP 100, MD 200, LCP 302, LCP 304, LCP 402, pulse generator 406, LCP 502 and pulse generator 506 may collect data pertaining to the patient's heart beat and rhythm. In some instances, it may be desirable to display this data, either real-time or later, for analysis and comparison. As illustrated for example with respect to FIGS. 3-5, these devices may be in different positions relative to each other and relative to the patient's heart. As a result, in some cases these devices may see a particular cardiac event from a different relative position and thus may see a particular cardiac event as occurring at a slightly different time. Accordingly, in some cases the cardiac event data from a first device may be temporally shifted relative to the cardiac event data (pertaining to the same event) from a second device. Moreover, one implantable device may "see" an event or signal with more specificity and clarity than another implantable device. For example, an LCP that is implanted with the heart itself may sense cardiac signals with more specificity and clarity than an SICD device that has subcutaneous sense electrodes that are positioned outside of the chest cavity. In this example, the LCP may sense the near field of the cardiac signal, while the SICD may sense the far field.

Figure 6:
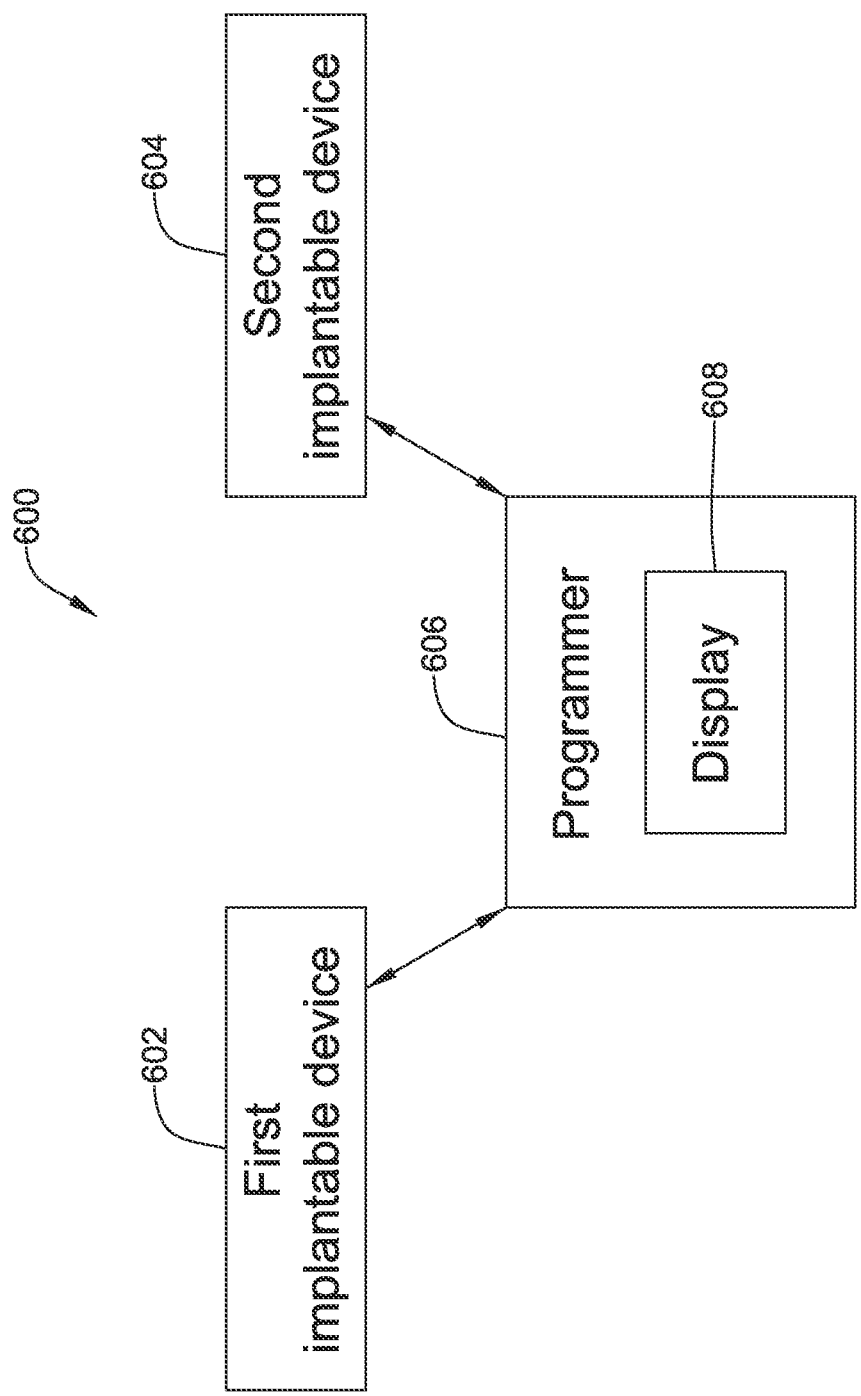
FIG. 6 is a schematic diagram of a system including a first implantable device and a second implantable device, according to an example of the present disclosure.

FIG. 6 is a schematic diagram of a system 600 that includes a first implantable device 602, a second implantable device 604 and a programmer 606. While identified as a programmer, element 606 may also be considered as being any of a non-implanted device, extracorporeal device or a non-implanted monitoring device. In some embodiments, a programmer or other non-implanted device may, for example, including a processor for processing data, memory for storing data and instructions, input/output devices for receiving and sharing data and other operational parameters, and the like. In some cases, a programmer or other non-implanted device may be included as part of a remote patient data monitoring system.

First implantable device 602 may be any implantable device, including those described with respect to FIGS. 1-5. Second implantable device 604 may be any implantable device, including those described with respect to FIGS. 1-5. In some embodiments, first implantable device 602 is an implantable defibrillator and second implantable device 604 is a leadless cardiac pacemaker, but this is not required. In some embodiments, programmer 606 is configured to communicate with first implantable device 602 and/or second implantable device 604. A variety of information may be communicated between programmer 606 and first implantable device 602 and/or between programmer 606 and second implantable device 604. In some embodiments, first implantable device 602 communicates directly with programmer 606 and second implantable device 604 communicates directly with programmer 606. In some instances, first implantable device 602 communicates directly with programmer 606 while second implantable device 604 communicates indirectly with programmer 606 through first implantable device 602. In some embodiments, first implantable device 602 may communicate directly with second implantable device 604. In some embodiments, first implantable device 602 and second implantable device 604 communicate indirectly with each other through programmer 606. In some instances, first implantable device 602 and second implantable device 604 do not communicate with each other.

In the example shown, programmer 606 includes a display 608. While a variety of different information may be displayed on display 608, it will be appreciated that temporal heart data emanating from first implantable device 602 and/or heart data emanating from second implantable device 604 may be temporally displayed on display 608. In some embodiments, the heart data emanating from first implantable device 602 is temporally shifted with respect to the heart data emanating from second implantable device 604. In some embodiments, the heart data emanating from first implantable device 602 may be displayed on display 608 in temporal alignment with the heart data emanating from second implantable device 604. In some embodiments, the heart data from each of first implantable device 602 and second implantable device 604 identifies the occurrence of one or more temporal events.

In some embodiments, programmer 606 is configured to display the heart data emanating from first implantable device 602 and second implantable device 604 in real or near real time. In this, real time may be defined as instantaneous with an event, or within several milliseconds after the event. Near real time may be defined as ranging from several milliseconds after the event to perhaps 10 or 20 milliseconds after the event. In some cases, the heart data emanating from first implantable device 602 and/or the heart data emanating from second implantable device 604 is stored data, and the stored heart data emanating from first implantable device 602 and/or the stored heart data emanating from second implantable device 604 is displayed at a later time. The heart data emanating from first implantable device 602 may, in some cases, include at least a portion of an electrocardiogram while the heart data emanating from second implantable device 604 may, in some cases, include a plurality of markers (sometimes without an electrocardiogram). The plurality of markers may include any number of markers including, for example, bradycardia/pacing markers and tachycardia/shocking markers.

Examples of bradycardia/pacing markers include VS (Ventricular Sense—After Refractory), [VS] (Ventricular Sense—Noise First Trigger), VS-Hy (Ventricular Sense—At Hysteresis Rate), VP (Ventricular Pace—Lower Rate or Atrial Tracked), VP↓ (Ventricular Pace—Rate Smoothing Down), VP↑ (Ventricular Pace—Rate Smoothing Up), VP-FB (Ventricular Pace—Fallback), VP-Hy (Ventricular Pace—At Hysteresis Rate), VP-Sr (Ventricular Pace—Sensor Rate), VP-Ns (Ventricular Pace—Noise) VP-Tr (Ventricular Pace—Trigger Mode) and VP-VR (Ventricular Pace—Ventricular Rate Regulation).

Examples of tachycardia/shock markers include PVC (PVC After Refractory), VT-1 (VT-1 Zone Sense), VT (VT Zone Sense), VF (VF Zone Sense), V-Epsd (Ventricular Tachy Start Episode), V-EpsdEnd (Ventricular Tachy End Episode), AFibV (V AFib Criteria Met), V-Dur (Duration Met), V-Detect (Ventricular Detection Met), Chrg (Start/End Charge), Dvrt (Therapy Diverted), Shock (Shock Delivered) and SRD (Sustained Rate Duration Expired).

Programmer 606 may temporally align the data from first implantable device 602 and second implantable device 604 in any suitable manner. In some embodiments, it is one of first implantable device 602 and second implantable device 604 that receives and temporally aligns its data with data received from the other of first implantable device 602 and second implantable device 604, then transmits the temporally aligned data to programmer 606 for display.

In some embodiments, for example, the heart data emanating from first implantable device 602 and/or the heart data emanating from second implantable device 604 includes a plurality of time stamps, and programmer 606 may be configured to use the plurality of time stamps to temporally align the heart data emanating from first implantable device 602 and the heart data emanating from second implantable device 604. In some embodiments, data emanating from first implantable device 602 may include a number of first time stamps, and data emanating from second implantable device 604 may include a number of second time stamps. Programmer 606 may utilize this number of first time stamps and number of second time stamps to temporally align the heart data.

In some embodiments, programmer 606 is configured to utilize one or more user-defined time delay parameters to temporally align the heart data emanating from first implantable device 602 and the heart data emanating from second implantable device 604. For example, there may be a consistent delay or time shift between data from first implantable device 602 and data from second implantable device 604, due for example to relative positions of first implantable device 602 and second implantable device 604, and/or due perhaps to communication delays between devices. In some cases, a user-defined time delay parameter may be inputted into programmer 606, which can then use the time delay parameter to help temporally align the heart data.

In some cases, the programmer 606 aligns the heart data. In other instances, the second implantable device 604 may receive heart data from the first implantable device 602 and then temporally align the heart data of the first implantable device 602 with the heart data of the second implantable device 604. The temporally aligned data may then be communicated from the second implantable device 604 to the programmer, wherein the temporally aligned data may be aligned with further heart data collected by the programmer if any, and displayed on a display of the programmer.

In some cases, the aligned data is displayed, stored and/or printed on a programmer. In other cases, the aligned data is displayed, stored and/or printed in a system that is remote from the patient, such as a remote patient management system. In some embodiments, the aligned data is displayed, stored and/or printed on a device used by the patient in a home or other non-clinical setting. While not programmers, these other devices may be used to display, store and/or print aligned data.

Figure 7:
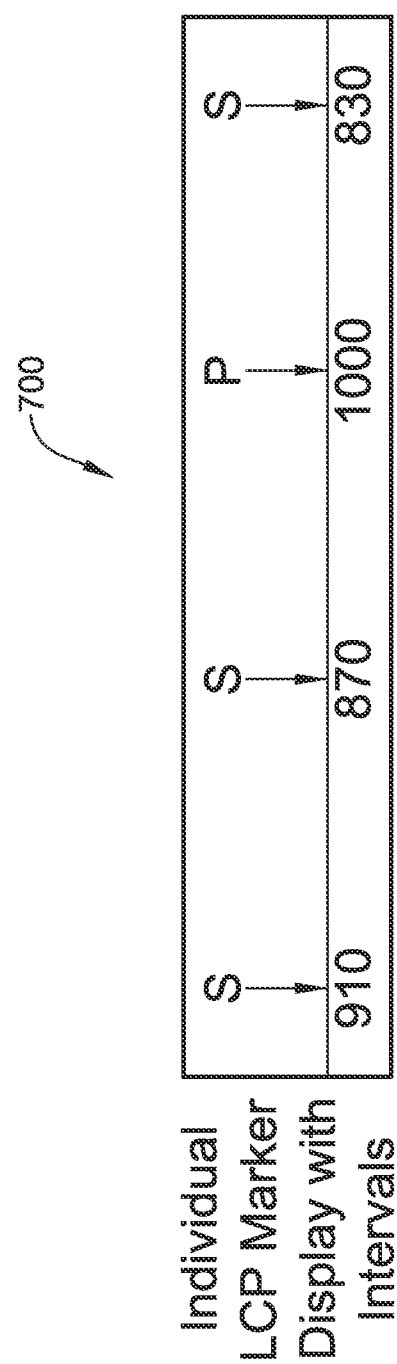
FIG. 7 is a diagram showing a display according to an example of the present disclosure.
Figure 8:
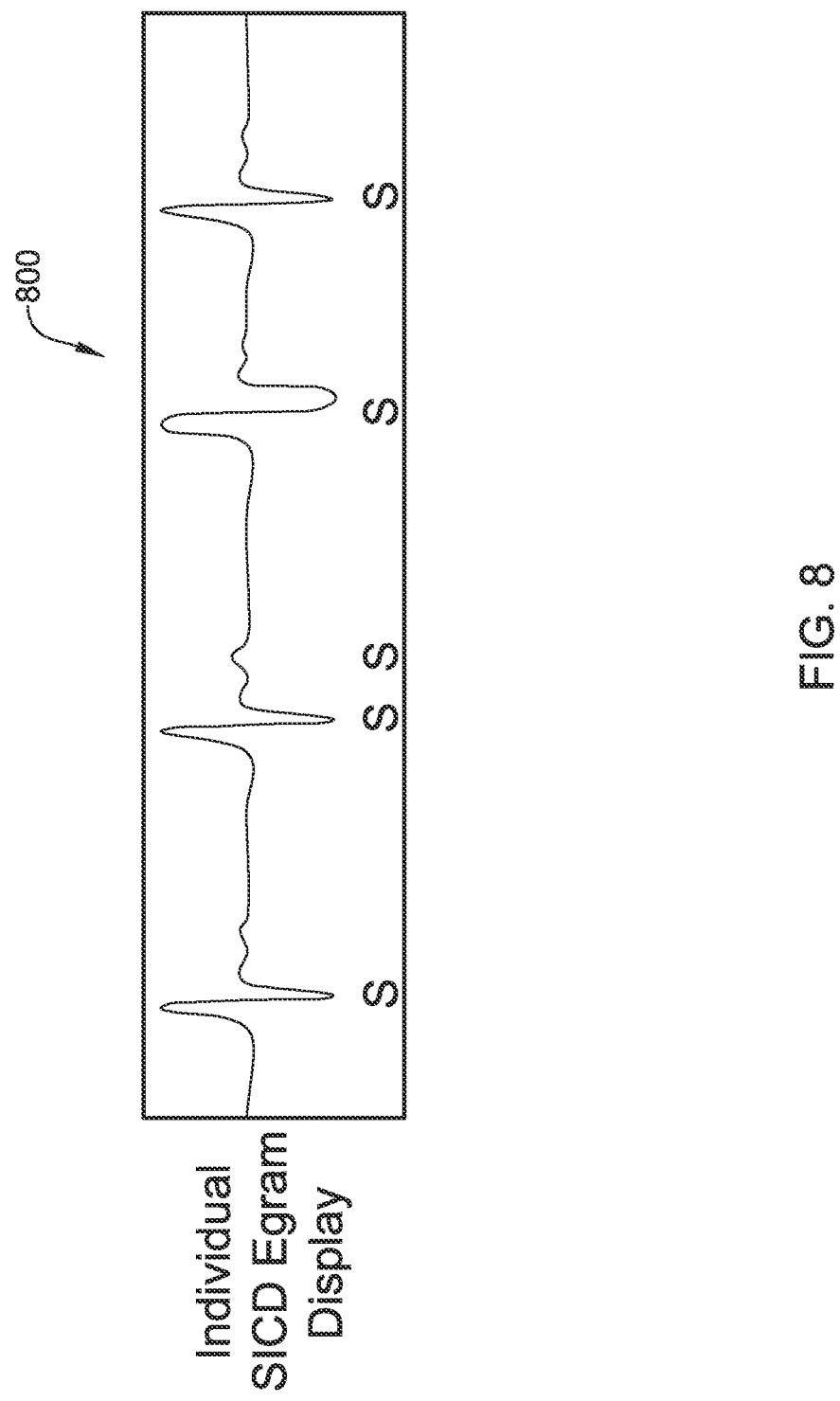
FIG. 8 is a diagram showing a display according to an example of the present disclosure.

FIGS. 7 through 11 provide examples of heart data that may be displayed via display 608 of programmer 606. FIG. 7 provides a display 700 of individual leadless cardiac pacemaker (LCP) markers. Display 700 may be seen as including several sense events, denoted with a marker "S", and a pace event, denoted with a marker "P". FIG. 8 provides a display 800 of an SICD egram of the same cardiac events shown in FIG. 7. Display 800 may be seen as including several sense events, denoted with a marker "S". Several points of interest in display 800 include an errant sense event, in which a T-wave is incorrectly read by the SICD as being a sense event (e.g. due to far field sensing of the SICD). Another point of interest is that the pace event detected by the LCP is interpreted by the SICD as a sense event.

Figure 9:
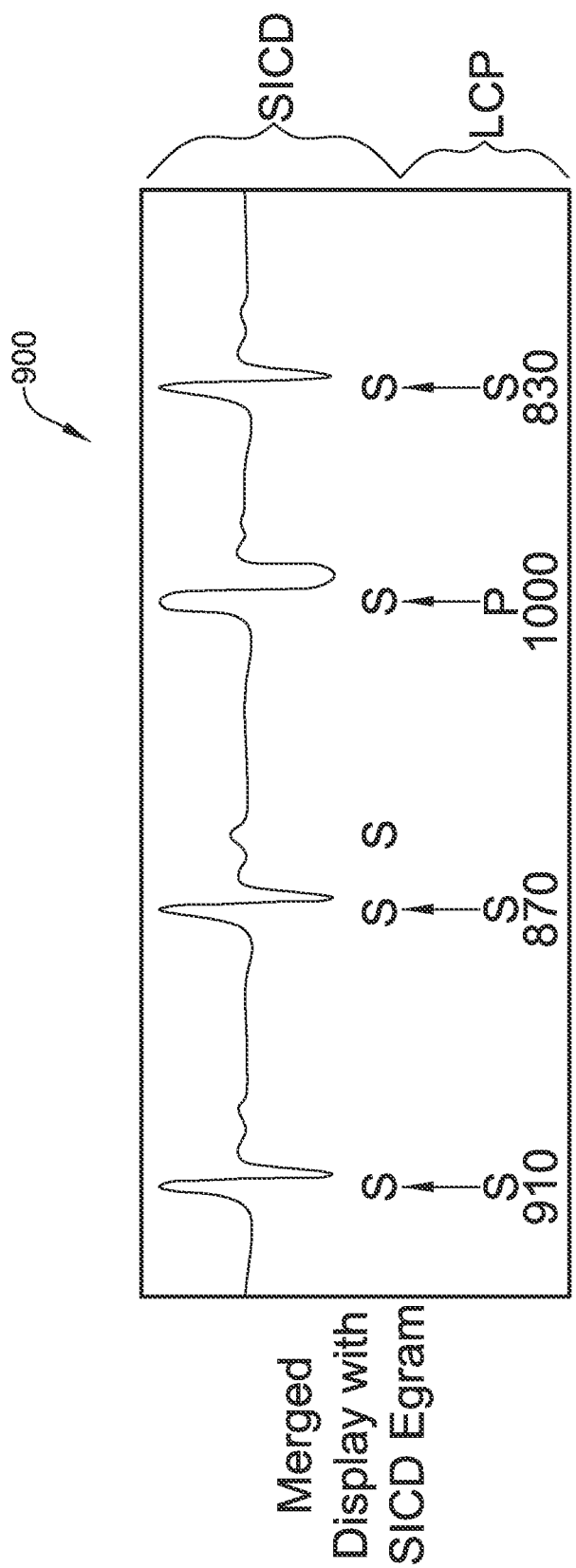
FIG. 9 is a diagram showing a display according to an example of the present disclosure.
Figure 10:
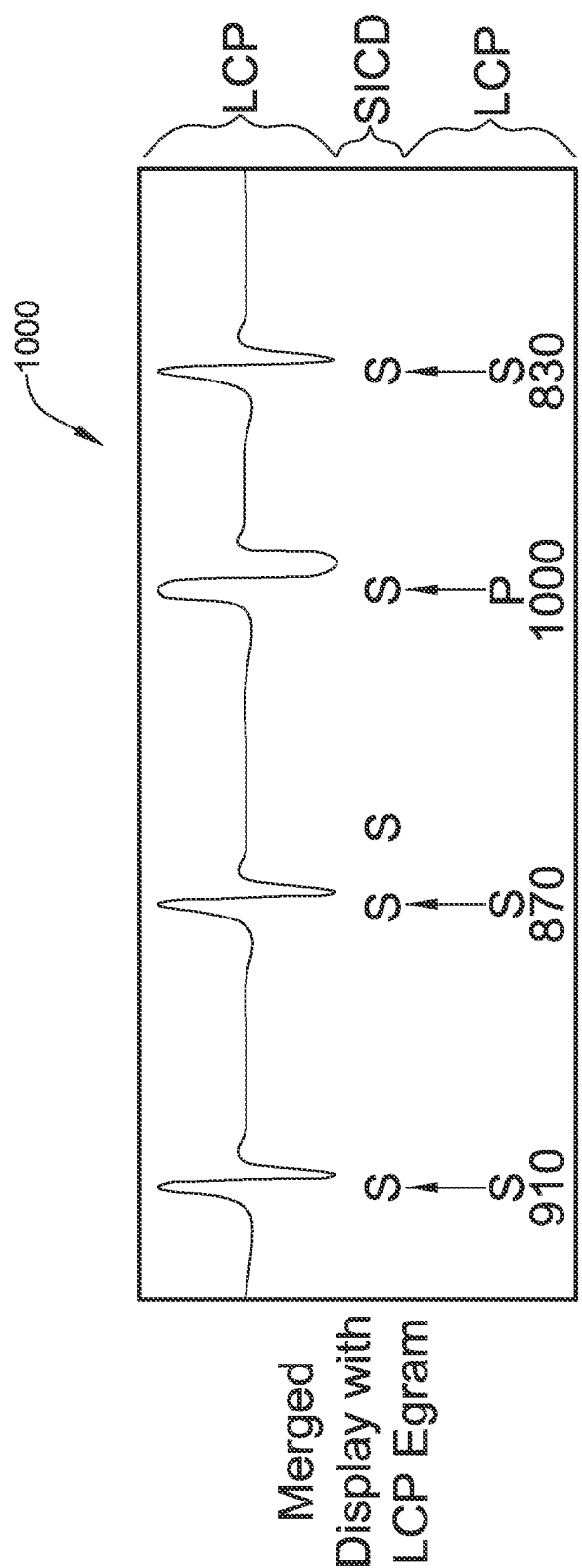
FIG. 10 is a diagram showing a display according to an example of the present disclosure.
Figure 11:
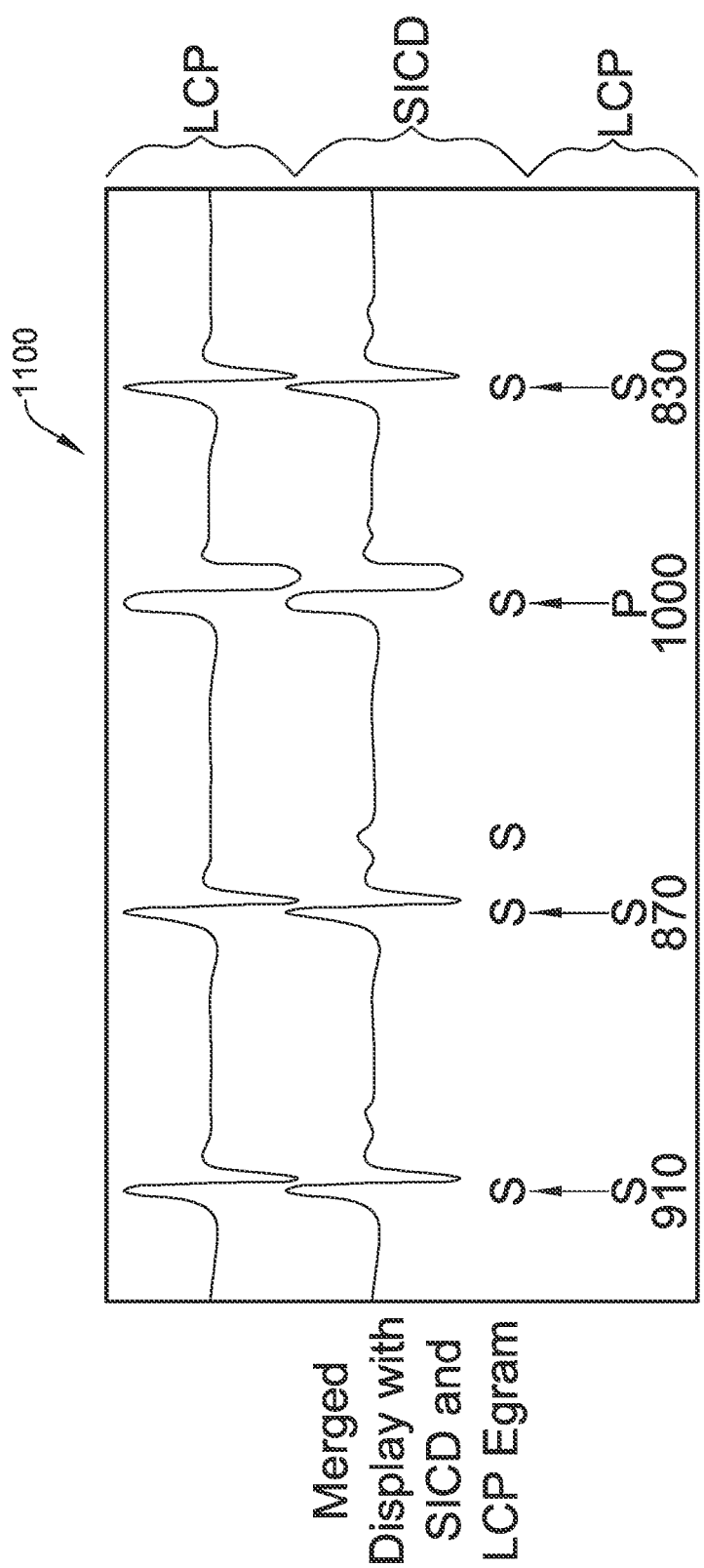
FIG. 11 is a diagram showing a display according to an example of the present disclosure.

FIG. 9 provides a display 900 that includes a combination of display 700 and display 800, with the heart data from the LCP (markers) temporally aligned with the heart data (electrocardiogram) from the SICD. It can be seen that the first sense event detected by the LCP temporally aligns with the first sense event detected by the SICD. By comparing the data from both devices on a single display, a physician or other professional can see that the later sense event detected by the SICD was actually a pace event as detected (and initiated) by the LCP. FIG. 10 is similar, but provides a display 1000 that shows an electrocardiogram and markers from the LCP compared with markers from the SICD. FIG.

11 provides a display 1100 that compares an electrocardiogram and markers from the LCP with an electrocardiogram and markers from the SICD.

It can be seen that display 608 may be used to display a variety of heart data emanating from first implantable device 602 and second implantable device 604. While data from two devices is illustrated, it will be appreciated that programmer 606 may be configured to temporally align and display heart data from any number of implantable devices, either in real-time or later displaying stored data.

In some cases, the aligned data relates to electrocardiograms and cardiac pace/sense markers. In other cases, the aligned data relates to other data acquired by implantable device 602 and/or implantable device 604. Examples of other data include markers for cardiac arrhythmias, markers for shock therapy or other markers indicating patient or device event. Yet other data may include trended data for cardiac conditions (e.g., atrial fibrillation, hypertension), pulmonary conditions (e.g., asthma), renal conditions (e.g., diabetes) or other patient conditions. Still other data may include data related to neural stimulation therapy, pharmaceutical therapy, and respiratory therapy (e.g., continuous positive airway pressure, CPAP).

Figure 12:
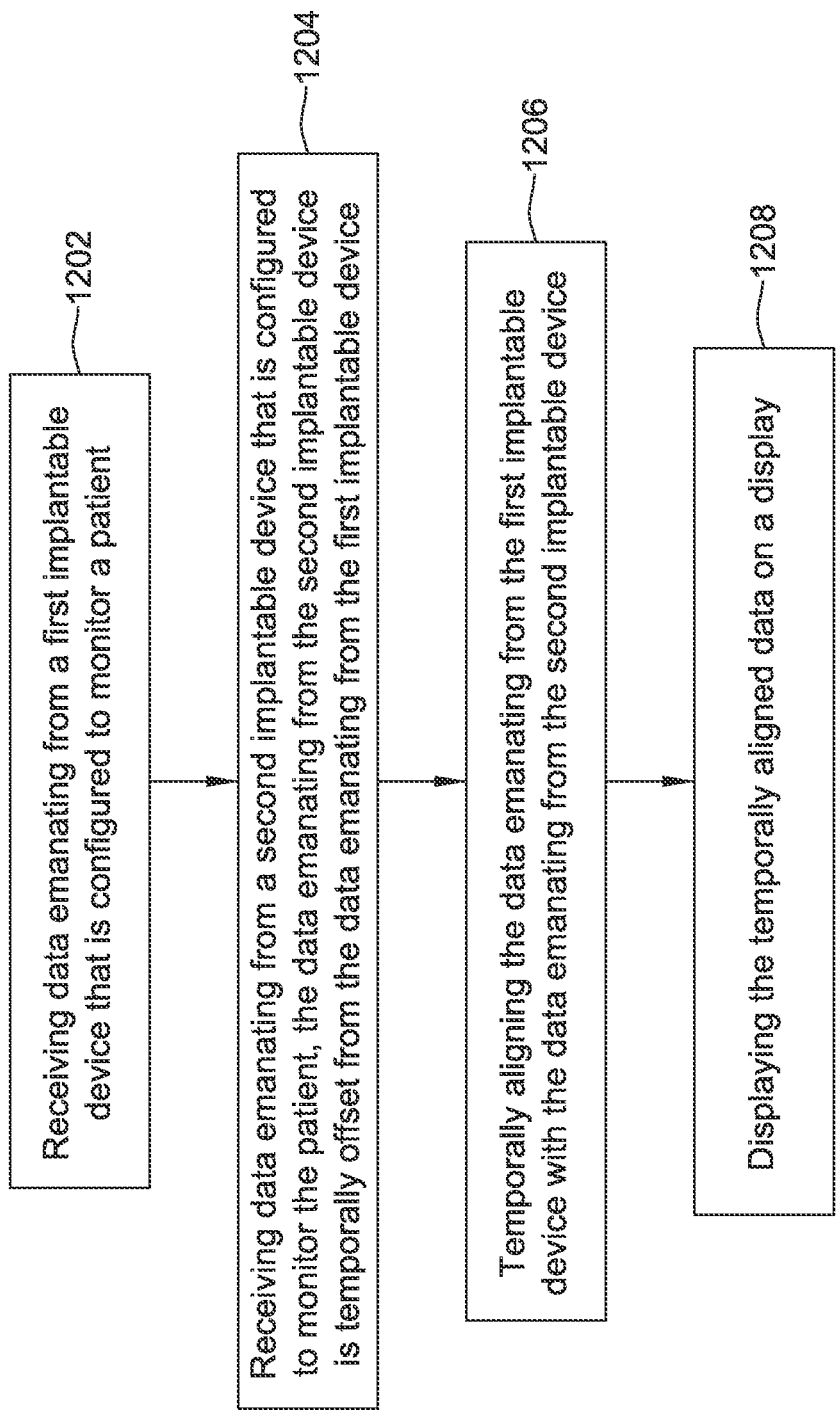
FIG. 12 is a flow diagram illustrating a method that may be carried out using any of the systems of FIGS. 1-6.

FIG. 12 is a flow diagram showing an illustrative method that may be carried out using the systems described herein. At block 1202, data emanating from a first implantable device configured to monitor a patient is received. In some embodiments, the data is heart data, but this is not required. Data emanating from a second implantable device that is configured to monitor the patient is received, as generally indicated at block 1204. The data (such as heart data) emanating from the second implantable device is temporally offset from the data (such as heart data) emanating from the first implantable device. In some embodiments, the first implantable device may be first implantable device 602 and the second implantable device may be second implantable device 604, but this is not required.

At block 1206, the data (such as heart data) emanating from the first implantable device is temporally aligned with the data (such as heart data) emanating from the second implantable device. In some embodiments, temporally aligning the data (such as heart data) emanating from the first implantable device with the data (such as heart data) emanating from the second implantable device includes using time stamp data included with either the data emanating from the first implantable device, the data emanating from the second implantable device, or both. In some embodiments, temporally aligning the data emanating from the first implantable device with the data emanating from the second implantable device includes using a user-defined delay value for data emanating from the second implantable device.

The temporally aligned data (such as heart data) is displayed on an extracorporeal display as generally indicated at block 1208. In some embodiments, displaying the temporally aligned data includes displaying at least a portion of an electrocardiogram emanating from the first implantable device, and simultaneously displaying one or more markers emanating from the second implantable device (sometimes without an electrocardiogram emanating from the second implantable device). In some embodiments, additional data may also be displayed.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A cardiac rhythm management system comprising:
an implantable defibrillator configured to sense cardiac activity of a patient's heart and provide shocking therapy if appropriate, the implantable defibrillator configured to output at least a portion of an electrocardiogram detected by the implantable defibrillator;
a leadless cardiac pacemaker configured to sense the cardiac activity of the patient's heart and provide pacing therapy if appropriate, the leadless cardiac pacemaker configured to determine a plurality of cardiac markers based on the sensed cardiac activity and output the plurality of cardiac markers;
a non-implanted device configured to receive and display heart data transmitted from the implantable defibrillator and from the leadless cardiac pacemaker, the heart data including at least a portion of an electrocardiogram and a plurality of cardiac markers; and
wherein the heart data transmitted from the leadless cardiac pacemaker and the heart data transmitted from the implantable defibrillator are displayed by the non-implanted device in temporal alignment so that the cardiac markers provided by the leadless cardiac pacemaker may be used to help verify one or more features of the electrocardiogram provided by the implantable defibrillator.

2. The cardiac rhythm management system of claim 1, wherein the heart data transmitted from the implantable defibrillator and/or the heart data transmitted from the leadless cardiac pacemaker is displayed by the non-implanted device in real or near real time.

3. The cardiac rhythm management system of claim 1, wherein the heart data transmitted from the implantable defibrillator is initially stored in the implantable defibrillator and/or the heart data transmitted from the leadless cardiac pacemaker is initially stored in the leadless cardiac pacemaker, and the stored heart data of the leadless cardiac pacemaker and the stored heart data of the implantable defibrillator is transmitted to and then displayed by the non-implanted device at a later time.

4. The cardiac rhythm management system of claim 1, wherein the heart data transmitted from the leadless cardiac pacemaker is communicated to the non-implanted device via the implantable defibrillator.

5. The cardiac rhythm management system of claim 1, wherein the heart data transmitted from the implantable defibrillator includes a number of first time stamps.

6. The cardiac rhythm management system of claim 5, wherein the heart data transmitted from the leadless cardiac pacemaker includes a number of second time stamps.

7. The cardiac rhythm management system of claim 6, wherein the non-implanted device is configured to use the first and second time stamps to temporally align the heart data transmitted from the implantable defibrillator and the heart data transmitted from the leadless cardiac pacemaker.

8. The cardiac rhythm management system of claim 1, wherein the non-implanted device is configured to utilize one or more user-defined time delay parameters to temporally align the heart data transmitted from the implantable defibrillator and the heart data transmitted from the leadless cardiac pacemaker.

9. A cardiac rhythm management system comprising:
a first implantable device configured to sense cardiac activity of a patient's heart and output heart data including at least a portion of an electrocardiogram representing electrical cardiac activity detected by the first implantable device;
a second implantable device configured to sense the cardiac activity of the patient's heart and output heart data including a plurality of markers that are based on the sensed cardiac activity;
a non-implanted device in communication with the first implantable device and the second implantable device, the non-implanted device configured to receive and display heart data outputted from the first implantable device and heart data outputted from the second implantable device, wherein the heart data outputted from the first implantable device and the heart data outputted from the second implantable device each identifies the occurrence of one or more temporal events; and
wherein the non-implanted device displays the heart data outputted from the second device and the heart data outputted from the first device in temporal alignment so that the plurality of markers provided by the second implantable device provide verification of one or more features of the electrocardiogram provided by the first implantable device.

10. The cardiac rhythm management system of claim 9, wherein the non-implanted device is further configured to display the heart data outputted from the first implantable device and the second implantable device in real or near real time.

11. The cardiac rhythm management system of claim 9, wherein the heart data outputted from the first implantable device and/or the heart data outputted from the second implantable device is initially stored by the first implantable device and/or the second implantable device, and the stored heart data of the first implantable device and/or the stored heart data of the second implantable device is transmitted to and then displayed by the non-implanted device at a later time.

12. The cardiac rhythm management system of claim 9, wherein the heart data outputted from the first implantable device and/or the heart data outputted from the second implantable device includes a plurality of time stamps, and the non-implanted device is configured to use the plurality of time stamps to temporally align the heart data outputted from the first implantable device and the heart data outputted from the second implantable device.

13. The cardiac rhythm management system of claim 9, wherein the non-implanted device is configured to utilize one or more user-defined time delay parameters to temporally align the heart data outputted from the first implantable device and the heart data outputted from the second implantable device.

14. A method of comparing heart rhythm data from a plurality of implantable medical devices, the method comprising:
receiving heart data emanating from a first implantable device that is configured to sense cardiac activity of a patient's heart, the heart data emanating from the first implantable device comprising at least a portion of an electrocardiogram;
receiving heart data emanating from a second implantable device that is configured to sense the cardiac activity of the patient's heart, the heart data emanating from the second implantable device comprising a plurality of cardiac markers that are based on the sensed cardiac activity, the heart data emanating from the second implantable device is temporally offset from the heart data emanating from the first implantable device;
temporally aligning the heart data emanating from the first implantable device and the heart data emanating from the second implantable device; and
displaying the temporally aligned heart data on a display.

15. The method of claim 14, wherein temporally aligning the heart data emanating from the first implantable device and the heart data emanating from the second implantable device comprises using time stamp data included with either the heart data emanating from the first implantable device, the heart data emanating from the second implantable device, or both.

16. The method of claim 14, wherein temporally aligning the heart data emanating from the first implantable device with the heart data emanating from the second implantable device comprises using a user-defined delay value for heart data emanating from the second implantable device.

17. The method of claim 14, wherein displaying the temporally aligned heart data comprises displaying at least a portion of the electrocardiogram emanating from the first implantable device and one or more of the plurality of cardiac markers emanating from the second implantable device.

* * * * *